(12) United States Patent
Ferreira et al.

(10) Patent No.: US 8,748,172 B2
(45) Date of Patent: Jun. 10, 2014

(54) CELL MODELING OF HEME DEFICIENCY USING FERROCHELATASE MUTATIONS

(71) Applicants: Gloria C. Ferreira, Tampa, FL (US); Zhen Shi, Pittsburgh, PA (US)

(72) Inventors: Gloria C. Ferreira, Tampa, FL (US); Zhen Shi, Pittsburgh, PA (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/033,012

(22) Filed: Sep. 20, 2013

(65) Prior Publication Data

US 2014/0087447 A1    Mar. 27, 2014

Related U.S. Application Data

(63) Continuation of application No. 11/741,354, filed on Apr. 27, 2007, now Pat. No. 8,586,530.

(60) Provisional application No. 60/745,811, filed on Apr. 27, 2006.

(51) Int. Cl.
*C12N 15/85* (2006.01)

(52) U.S. Cl.
USPC .......................................... 435/325; 536/23.1

(58) Field of Classification Search
None
See application file for complete search history.

(56) References Cited

U.S. PATENT DOCUMENTS

| 4,879,237 A | 11/1989 | Rudslahti et al. |
| 7,008,937 B2 | 3/2006 | Bommer |
| 2003/0131363 A1 | 7/2003 | Chen |

OTHER PUBLICATIONS

Lecerof, D., Fodje, M., Hansson, A., Hansson, M., and Al-Karadaghi, S. 2000. Structural and mechanistic basis of porphyrin metallation by ferrochelatase. J. Mol. Biol. 297: 221-232.
Sigfridsson, E., and Ryde, U. 2003. The importance of porphyrin distortions for the ferrochelatase reaction. J. Biol. Inorg. Chem. 8: 273-282.
Venkateshrao, S., Yin, J., Jarzecki, A.A., Shultz, P.G. and Spiro, T.G.2004. Porphyrin distortion during affinity maturation of a ferrochelatase antibody, monitored by Resonance Raman spectroscopy. J. Am. Chem. Soc. 126: 16361-16367.
Abbas, A., and Labbe-Bios, R. 1993. Stucture-Function Studies of Yeast Ferrochelatase. J. Biol. Chem. 268: 8541-8546.
Atamna, H. 2004. Herne, iron, and the mitochondrial decay of ageing. Ageing Research Reviews. 3: 303-318.
Campian, J. L., Qian, M., Gao, X., and Eaton, J. W. 2004. Oxygen Tolerance and Coupling of Mitochondrial Electron Transport. J. Biol. Chem. 279: 46580-46587.
Childs, S., Weinstein, B. M., Mohideen, M. P. K., Donohue, S., Bonkovsky, H., and Fishman, M. C. 2000. *Zebrafish dracula* encodes ferrochelatase and its mutation provides a model for erythropoietic protoporphyria. Current Biolog. 10: 1001-1004.
Combet, C., Jambon, M., Deleage, G., and Geourjon, C. 2002. Geno3D: automatic comparative molecular modeling of protein. Bioinformatics Applications Note. 18: 213-214.
Hambright, P., and Chock, P. B. 1973. Metal-Porphyrin Interactions. Journal of the American Chemical Society. 96: 3123-3131.
Kimmett, S. M., Whitney, R. A., and Marks, G. S. 1992. Evidence for the Stereoselective Inhibition of Chick Embryo Hepatic Ferrochelatase by N-Alkylated Porphyrins, II. Molecular Pharmacology. 42: 307-310.
Liang, J., Edelsbrunner, H., and Woodward, C. 1998. Anatomy of protein pockets and cavities: Measurements of binding site geometry and implications for ligand design. Protein Science. 7: 1884-1897.
Mallis, R. J., Brazin, K. N., Fulton, D. B., and Andreotti, A. H. 2002. Structural characterization of a proline-driven conformational switch within the Itk SH2 domain. Nature Structural Biology. 9: 900-905.
Nemeria, N., Yan, Y., Zhang, Z., Brown, A. M., Arjunan, P., Furey, W., Guest, J. R., and Jordan, F. 2001. Inhibition of the *Escherichia coli* Pyruvate Dehydro genase Complex E1 sub unit and Its Tyrosine 177 Variations by Thiamin 2-Thiazolone and Thiamin 2-Thiothiazolone Diphosphates. J. Biol. Chem. 276: 45969-45978.
Tangeras, A. 1986. Effect of decreased ferrochelatase activity on iron and porphyrin content in mitochondria of mice with porphyria induced by griseofulvin. Biochimica et Biophysica Acta. 882: 77-84.
Dailey, H. A., and Dailey, T. A. 2003. Ferrochelatase. The Porphyrin Handbook. 12: 93-121.
Vogel, M., Bukau, B., and Mayer, M. P. 2006. Allosteric Regulation of Hsp70 chaperones by a Proline Switch. Molecular Cell. 21: 359-367.
Anderson, K. S., Sikorski, J. A., and Johnson, K. A. 1988. Evaluation of 5-Enolpyruvoylshikimate -3-phosphate synthase substrate and Inhibitor Binding by Stopped-Flow and Equilibrium Fluorescence Measurements. Biochemistry. 28: 1604-1610.
Blackwood, M. E., Rush III, T. S., Romesberg, F., Schultz, P. G., and Spiro, T. G. 1998. Alternative Modes of Substitute Distribution in Enzyme and Antibody Catalyzed Ferrochelation Reactions. Biochemistry. 37: 779-782.
Caughey, W. S., and Iber, P. K. 1963. Ring Nonplanarity and Aromaticity in Porphrins. Nuclear Magnetic Resonance Spectra of Etioporphyrin II and Its N-Alkyl Compounds. Department of Physiological Chemistry, The Johns Hopkins School of Medicine, and the Department of Chemistry, The Johns Hopkins University, Baltimore, Maryland. 28: 269-270.

(Continued)

*Primary Examiner* — Anand Desai
(74) *Attorney, Agent, or Firm* — Robert J. Varkonyi; Smith & Hopen, P.A.

(57) ABSTRACT

Provided herein, is a means for development of ferrochelatase variants with improved tolerance towards N-methyl protoporphyrin. Also disclosed are cell assay systems utilizing the variants, as the variants would confer resistance to N-methyl protoporphyrin inhibition and thereby keep heme synthesis uninterrupted. The variants contain loop mutations that affect the NMPP-ferrochelatase interaction, and different degrees of NMPP tolerance are obtained with the introduction of loop mutations in wild-type ferrochelatase. Also disclosed is kinetic mechanism of inhibition of ferrochelatase by NMPP, using the disclosed variants whose mutations in the "porphyrin-interacting loop" motif weakened the potency of NMPP as an inhibitor.

7 Claims, 5 Drawing Sheets

(56) References Cited

OTHER PUBLICATIONS

Cochran, A. G., and Schultz, P. G. 1990. Antibody-Catalyzed Porphyrin Metallation. Science. 249: 781-783.

Gora, M., Grzybowska, E., Rytka, J., and Labbe-Bois, R. 1996. Probing the Active-site Residues in *Saccharomyces cerevisiae* Ferrochelatase by Directed Mutagenesis. J. Biol. Chem. 271: 11810-11816.

Houghton, J. D., Honeybourne, C. L., Smith, K. M., Tabba, H. D., and Jones, O. T. G. 1982. The use of N-methylprotoporphyrin dimethyl ester to inhibit ferrochelatase in *Rhodopseudomonas sphaeroides* and its effect in promoting biosynthesis of magnesium terapyrroles. Biochem. J. 208: 479-486.

Lewis, S. D., Lucas, B. J., Brady, S. F., Sisko, J. T., Cutrona, K. J., Sanderson, P. E. J., Freidinger, R. M., Mao, S., Gardell, S. J., and Shafer, J. A. 1998. T. Biol. Chem. 273: 4843-4854.

Magness, S. T. and Brenner, D. A. 1999. Targeted disruption of the mouse ferrochelatase gene producing and exon 10 deletion. Biochimica et Biophysica Acta. 1453: 161-174.

Nakahigashi, K., Nishimura, K., Miyamoto, K., and Inokuchi, H. 1991. Photosensitivity of a protoporphyrin-accumulating, light-sensitive mutant (visA) of *Escherichia coli* K-12. Proc. Natl. Acad. Sci. 88: 10520-10524.

Williams, J. W., and Morrison, J. F. 1979. The Kinetics of Reversible Tight-Binding Inhibition. Methods in Enzymology. 63: 437-467.

Kohno, H., Okuda, M., Furukawa, T., Tokunaga, R., and Taketani, S. 1994. Site Directed Mutagenesis of human ferrochelatase: Identification of histidine-263 as a binding site for metal ions. Biochimica et Biophysica Acta. 1209: 95-100.

Schoenfeld, R. A., Napoli, E., Wong, A., Zhan, S., Reutenauer, L., Morin, D., Buckpitt, A. R., Taroni, F., Lonnerdal, B., Ristow, M., Puccio, H., and Cortopassi, G. A. 2005. Frataxin deficiency alters heme pathway transcripts and decreases mitochondrial heme metabolites in mammalian cells. Human Molecular Genetics. 14: 3787-3799.

Yin, J., Andryski, S. E., Beuscher, A. E., Stevens, R. C., and Schultz, P. G. 2003. Structural evidence for substrate strain in antibody catalysis. PNAS. 100: 856-861.

| | | | | | | | | | | | |
|---|---|---|---|---|---|---|---|---|---|---|---|
| Mus musculus | Q | S | K | V | G | - | - | P | V | P | W | L |
| Homo sapiens | Q | S | K | V | G | - | - | P | M | P | W | L |
| Gallus gallus | Q | S | K | V | G | - | - | P | M | P | W | L |
| Drosophila melanogaster | Q | S | K | V | G | - | - | P | L | A | W | L |
| Arabidopsis thaliana | Q | S | R | V | G | - | - | P | V | Q | W | L |
| Hordeum vulgare | Q | S | R | V | G | - | - | P | V | Q | W | L |
| Saccharomyces cerevisiae | Q | S | Q | V | G | - | - | P | K | P | W | L |
| Schizosaccharomyces pombe | Q | S | K | V | G | - | - | P | L | P | W | M |
| Escherichia coli | Q | S | R | F | G | - | - | R | E | P | W | L |
| Yersinia enterocolitica | Q | S | R | F | G | - | - | R | E | P | W | L |
| Thermus thermophilus | Q | S | - | A | G | R | T | P | E | P | W | L |
| Bacillus subtilis | Q | S | E | - | G | N | T | P | D | P | W | L |

B.

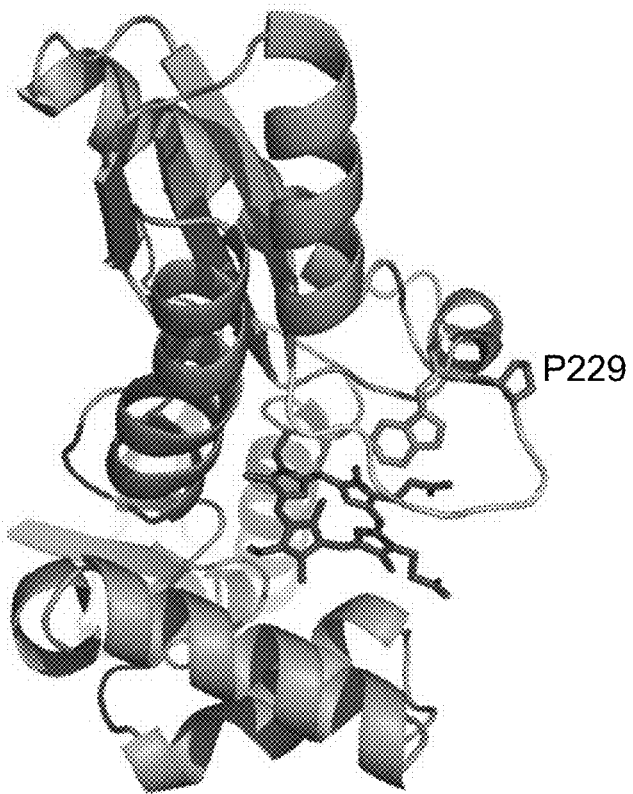

P229

Figure 3
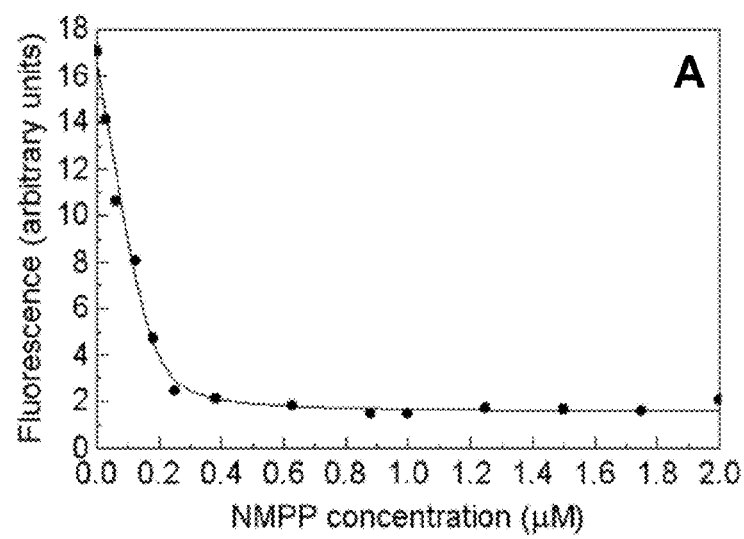
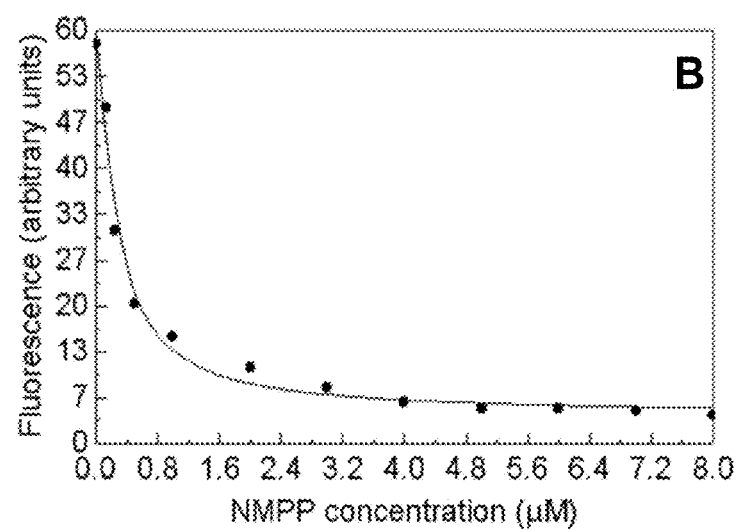
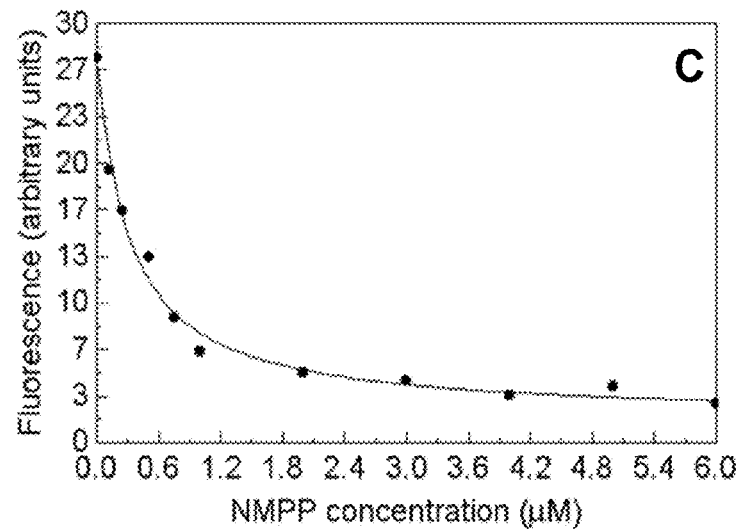

US 8,748,172 B2

CELL MODELING OF HEME DEFICIENCY USING FERROCHELATASE MUTATIONS

CROSS REFERENCE TO RELATED APPLICATIONS

This application is a continuation of U.S. patent application Ser. No. 11/741,354, entitled "Modulation of Inhibition of Ferrochelatase by N-Methyl Protoporphyrin", filed Apr. 27, 2007, which claims priority to U.S. Provisional Patent Application No. 60/745,811, entitled "Modulation of Inhibition of Ferrochelatase by N-Methyl Protoporphyrin" filed Apr. 27, 2006, which is herein incorporated by reference.

STATEMENT OF FINANCIAL SUPPORT

This invention was made with support from the American Cancer Society under Grant No. RSG-96-05106-TBE.

FIELD OF INVENTION

This invention relates to a means for development of ferrochelatase variants with improved tolerance towards N-methyl protoporphyrin.

BACKGROUND OF THE INVENTION

Protoporhyrin IX ferrochelatase (protoheme ferrolyase, E.C. 4.99.1.1; hereafter referred to as ferrochelatase), the terminal enzyme of the heme biosynthetic pathway, catalyzes the insertion of ferrous iron into protoporphyrin IX to yield protoheme. Distortion of the porphyrin macrocycle has long been recognized to be a critical step in porphyrin metallation. Porphyrin distortion heightens metal chelation by endowing porphyrin with an appropriate configuration for metal ion complexation. In this configuration, the lone-pair orbitals of the pyrrole nitrogens are exposed to the incoming metal ion.

Protoporhyrin IX ferrochelatase catalyzes the terminal step of the heme biosynthetic pathway by inserting ferrous iron into protoporphyrin IX. N-methyl protoporphyrin (NMPP), a transition-state analog and potent inhibitor of ferrochelatase, is commonly used to induce heme deficiency in mammalian cell cultures.

SUMMARY OF INVENTION

To create ferrochelatase variants with different degrees of tolerance towards NMPP and further understand the mechanism of ferrochelatase inhibition by NMPP, the inventors isolated variants with increased NMPP-resistance bearing mutations in an active site loop (murine ferrochelatase residues 248-259), which was previously shown to mediate a protein conformational change triggered by porphyrin binding. The kinetic mechanisms of inhibition of two variants, in which P255 was replaced with either arginine (P255R) or glycine (P255G), were investigated and compared to that of wild-type ferrochelatase. While the binding affinity of the P255 variants for NMPP decreased by one order of magnitude in relation to that of wild-type enzyme, the inhibition constant increased by approximately two orders of magnitude ($K_i^{app}$ values of 1 μM and 2.3 μM for P255R and P255G, respectively, vs. 3 nM for wild-type ferrochelatase). Nonetheless, the drastically reduced inhibition of the variants by NMPP was not paralleled with a decrease in substrate specificity ($k_{cat}/K_m^{PPIX}$) and/or catalytic activity ($k_{cat}$). Further, although NMPP binding to either wild-type ferrochelatase or P255R occurred via a similar, two-step kinetic mechanism, the forward and reverse rate constants associated with the second and rate-limiting step were comparable for the two enzymes. Collectively, these results show that P255 has a crucial role in maintaining an appropriate protein conformation and modulating the selectivity and/or regiospecificity of ferrochelatase.

N-methyl protoporphyrin (NMPP), a potent inhibitor of ferrochelatase [$K_i$~10 nM], resembles a strained substrate, and it is precisely this non-planarity of the porphyrin ring that has been generally accepted to confer the inhibitory properties of the alkylated porphyrin. Here, the inventors show that loop mutations affect the NMPP-ferrochelatase interaction, and different degrees of NMPP tolerance can be obtained with the introduction of loop mutations in ferrochelatase. Towards understanding the molecular basis for the effectiveness of NMPP as an inhibitor of ferrochelatase, here, the inventors show the kinetic mechanism of inhibition of ferrochelatase by NMPP, by focusing on variants whose mutations in the "porphyrin-interacting loop" motif weakened the potency of NMPP as an inhibitor.

An out-of-plane distortion occurs upon porphyrin binding to ferrochelatase and this induced distortion is energetically favorable. Further, the tilting of one of the pyrroles lowers the energy of metal insertion by about 50 kJ mol$^{-1}$. In particular, the crystal structure of the complex between ferrochelatase and N-methyl mesoporphyrin reveals a largely saddled-ruffled structure, with a tilt angle in relation to the mean porphyrin plane of approximately 36° for pyrrole ring A and approximately 5° for the other three pyrrole rings. While most of the distortion certainly results from the N-methyl substitution, the high selectivity and affinity of ferrochelatase for this porphyrin conformation suggest that it is the favored distorted structure adopted by the protein-bound porphyrin substrate and corroborates the notion that N-methyl porphyrins are transition state analogues for porphyrin metallation. In fact, antibodies elicited to non-planar N-methyl porphyrins catalyze metal ion incorporation into porphyrin. Significantly, the mode and extent of the ferrochelatase-induced distortion of the porphyrin substrate were recently proposed to enhance the reaction rate by decreasing the activation energy of the reaction and control the metal ion selectivity by modulating which divalent metal ion is incorporated into the porphyrin ring.

The importance of a conserved, active site loop motif (FIG. 1) in the interaction between ferrochelatase and protoporphyrin has been assessed using a combination of random mutagenesis and steady-state kinetic analysis. While multiple functional substitutions were tolerated within the 10 amino acid-loop motif, the positions occupied by Q248, S249, G252, W256 and L257 exhibited high informational content, as permissible substitutions were limited and only observed in multiply substituted variants. Strikingly, resonance Raman spectroscopy studies indicated that the degree of a specific non-planar porphyrin deformation contributed to the catalytic efficiency of ferrochelatase and loop variants. When compared to the wild-type enzyme, the reduced non-planar porphyrin deformation (saddling) associated with the variants correlated with their decreased catalytic efficiencies towards porphyrin. Indeed, one variant with a catalytic efficiency one order of magnitude lower than that of wild-type enzyme produced less than 30% of the wild-type saddling deformation. The loop residues also appeared to orient, specifically, the porphyrin vinyl substituents and likely the entire porphyrin macrocycle.

Ferrochelatase, the terminal enzyme of the heme biosynthetic pathway is strongly inhibited by N-methylprotoporphyrin. The disclosed invention provides a means for development of ferrochelatase variants with improved tolerance towards N-methylprotoporphyrin, which could be potentially used in cell assay systems to study physiological responses to heme deficiency.

This invention provides a means for development of ferrochelatase variants with improved tolerance towards N-methyl protoporphyrin. Specific applications include their use in cell assay systems, as the variants would confer resistance to N-methyl protoporphyrin inhibition and thereby keep heme synthesis uninterrupted.

The invention provides a means whereby ferrochelatase variants with improved tolerance towards N-methyl protoporphyrin can be potentially used in cell assay systems to study physiological responses to heme deficiency. It should be possible to determine whether the commonly observed N-methyl protoporphyrin-induced cytotoxicity could be alleviated by expressing constitutively P255 variants (e.g., P255R and P255G); these variants would confer resistance to N-methyl protoporphyrin inhibition and thereby keep heme synthesis uninterrupted.

This invention provides a means for development of ferrochelatase variants with improved tolerance towards N-methyl protoporphyrin. Specific applications include their use in cell assay systems, as the variants would confer resistance to N-methyl protoporphyrin inhibition and thereby keep heme synthesis uninterrupted.

The invention provides a tool entailing ferrochelatase variants with increased tolerance towards N-methyl protoporphyrin. These variants would permit investigators to work with cell assay systems bypassing the toxicity introduced with N-methyl protoporphyrin and heme biosynthesis inhibition.

Research and clinical laboratories working with cell cultures require inhibition of heme synthesis without subsequent cell toxicity. Heme deficiency has been recently reported to be associated with various disorders, such as Alzheimer's disease, frataxin-deficiency mediated diseases and oxidative damage resulted from hyperoxia. In these studies, N-methyl protoporphyrin treatment of cultured cells has provided a convenient model system to induce heme deficiency. Typically, N-methyl protoporphyrin-treated cells exhibit impaired enzymatic activity and assembly of the mitochondrial electron transport complex IV, i.e., cytochrome c oxidase (COX). COX has been proposed to have a cytoprotective role by removing reactive oxygen species and its deficiency renders cells more susceptible to oxidative stress. Thus, the P255-directed ferrochelatase variants with improved tolerance towards NMPP have utility in cell assay systems to study physiological responses to heme deficiency.

BRIEF DESCRIPTION OF THE DRAWINGS

For a fuller understanding of the invention, reference should be made to the following detailed description, taken in connection with the accompanying drawings, in which:

FIG. 1 shows the Porphyrin-interacting loop motif in ferrochelatase. A. Amino acid sequence alignment of porphyrin-interacting loop motif residues; *Mus musculs*, SEQ ID NO. 1; *Homo sapiens*, SEQ ID NO: 2; *Gallus gallus*, SEQ ID NO: 3; *Drosophila melanogaster*, SEQ ID NO:4; *Arabidopsis thaliana*, SEQ ID NO: 5; *Hordeum vulgare*, SEQ ID NO: 6; *Saccharomyces cerevisiae*, SEQ ID NO: 7; *Schizosaccharomyces pombe*, SEQ ID NO 8; *Escherichia coli*, SEQ ID NO: 9; *Yersinia enterocilitica*, SEQ ID NO: 10; *Thermus thermophilus*, SEQ ID NO: 11; and *Bacillus subtilis*, SEQ ID NO: 12. P255 in murine ferrochelatase, which was analyzed in this study, and its homologs, are boxed. B. *B. subtilis* ferrochelatase active site in a complex with N-methyl mesoporphyrin (Protein data base code 1C1H). P229 and W230 (the homologs of P255 and W256 in murine ferrochelatase) are shown in ball-and-stick form. W230 is shown in close proximity to ring C of N-methyl mesoporphyrin (Lecerof et al. 2000; Shi et al. 2006). The figure is labeled as follows: gray tube, porphyrin-interacting loop motif (Q221-L231 and Q248-L257, *B. subtilis* and murine ferrochelatase numbering, respectively); dark gray ball-and-sticks, N-methyl mesoporphyrin; medium gray ball-and-sticks, P229; gray ball-and-sticks, W230. Coordinates of the crystal structure were obtained from the Protein Data Bank (Research Collaboratory for Structural Bioinformatics) and displayed using SwissPDB viewer v3.7 software (Swiss Institute of Bioinformatics, Lausanne, Switzerland).

FIG. 3 shows the fluorescence titration of NMPP binding to either wild-type ferrochelatase or P255 variants. Aliquots of NMPP were added to a solution of enzyme in 10 mM Tris-acetate, pH 8 containing 0.05% Tween-80 and incubated on ice for 1 hr. The intrinsic protein fluorescence was monitored at 331 nm ($\lambda_{ex}$=283 nm). The $K_d$ value for NMPP was determined by fitting the data to Equation 3. The enzymes used in each set were: A. wild-type ferrochelatase (40 nM); B. P255R (250 nM); C. P255G (120 nM).

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

NMPP has long been known to be a potent inhibitor of mammalian ferrochelatase, which competes with the porphyrin substrate for binding to the enzyme. Since alkylation of a pyrrole nitrogen introduces non-planarity into the porphyrin macrocycle, the inhibitory properties of NMPP are thought to arise from its structural resemblance to the distorted porphyrin intermediate in the ferrochelatase-catalyzed reaction. In addition, the analysis of the X-ray crystal structural of *B. subtilis* ferrochelatase complexed with N-methyl mesoporphyrin indicated that the active site loop residues are in close proximity to the porphyrin macrocycle. This observation led us to hypothesize that different mutations in the loop motif should modulate binding of N-alkylated porphyrins and consequently control their potency as inhibitors of ferrochelatase. In order to test this hypothesis, selected loop variants were examined with respect to the kinetics of inhibition by NMPP. Also, ferrochelatase variants with different degrees of tolerance towards NMPP could be instrumental in cell culture systems designed to model heme deficiency, as the use of NMPP to inhibit ferrochelatase and heme biosynthesis is generally accompanied with cellular toxicity.

Isolation of Ferrochelatase Loop Variants with Increased Resistance to NMPP.

To isolate *Escherichia coli* Δvis transformants harboring loop variants more tolerant to NMPP than wild-type ferrochelatase, 33 variants isolated from a library of 214 functional, ferrochelatase clones were plated on LB-ampicilin medium containing 0.2 µM, 2 µM or 20 µM NMPP. *E. coli* Δvis cells can only grow when hemin is added to the medium or when the cells are transformed with an active ferrochelatase expression plasmid. Transformants harboring a subset of the functional loop variants including K250N, V251L, P255R, P255G, K250M/V251L/W256Y and Q248P/S249G/K250P/G252W were grown onto LB-ampicilin plates with increasing concentrations of NMPP. While Δvis cells expressing variants P255R and P255G could form colonies onto medium containing more than 20 µM NMPP, Δvis cells transformed with either wild-type ferrochelatase or the other variants could not. Based on this observation, the P255 variants were selected for further characterization.

Equilibrium Binding of NMPP to Ferrochelatase.

Figure 2:
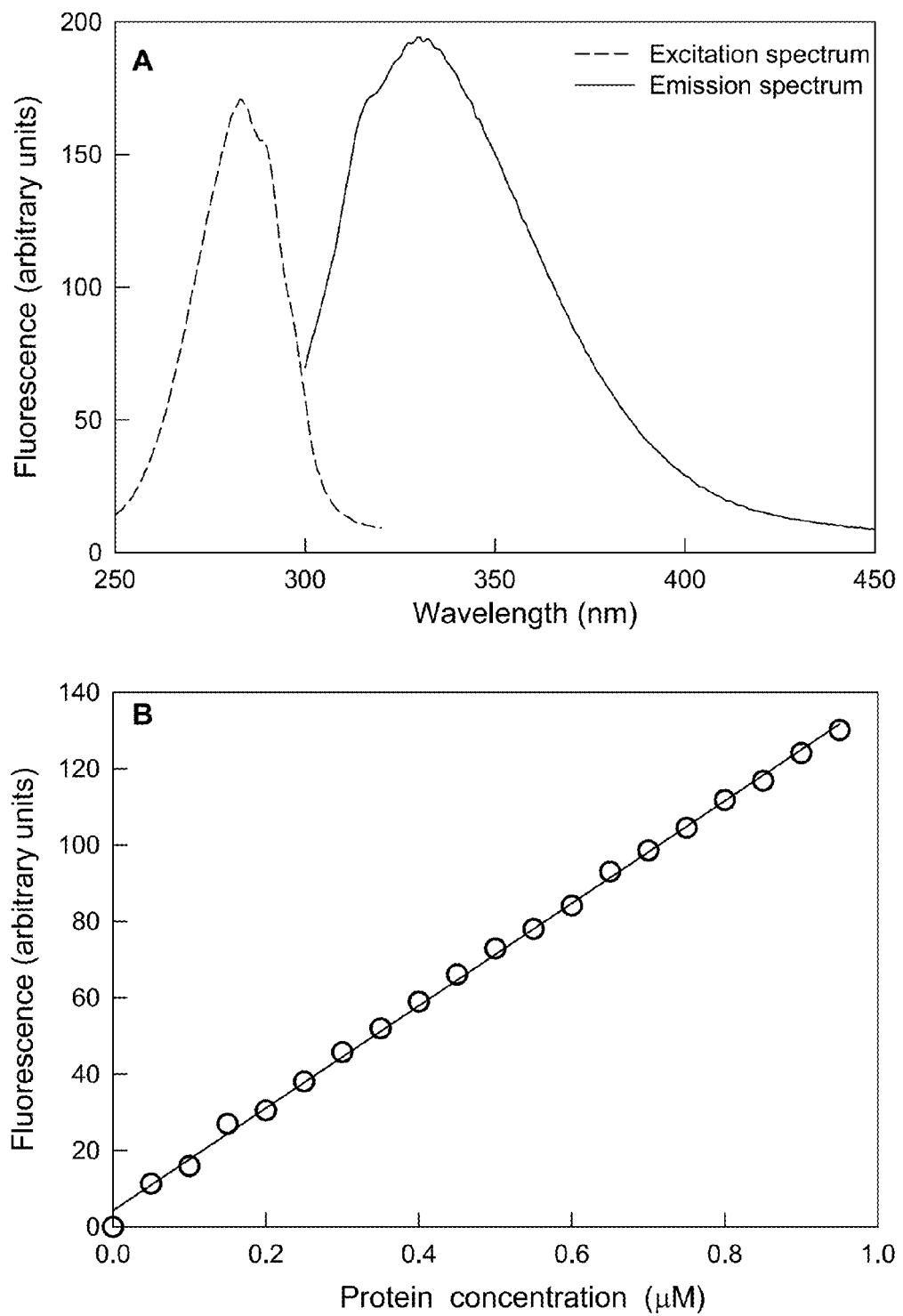
FIG. 2 shows the intrinsic fluorescence of ferrochelatase. A. Fluorescence excitation and emission spectra of wild-type, murine ferrochelatase are shown for 0.9 µM enzyme in 10 mM Tris-acetate containing 0.05% Tween-80. The emission spectrum exhibits a maximum at 331 nm ($\lambda_{ex}$=283 nm), while the excitation spectrum displays a maximum at 283 nm ($\lambda_{em}$=331 nm). B. The intrinsic protein fluorescence is proportional to enzyme concentration. Fluorescence of wild-type, murine ferrochelatase was measured at 331 nm ($\lambda_{ex}$=283 nm).

Tryptophan is a major contributor to intrinsic protein fluorescence, and thus quenching of tryptophan fluorescence is frequently used for detection of changes in the local environment of the fluorophore upon ligand binding. In wild-type, murine, mature ferrochelatase, five tryptophan residues (two of them being in the active site) contributed to the intrinsic protein fluorescence, which exhibited an excitation maximum at ~280 nm ($\lambda_{em}$=331 nm) and an emission maximum at ~330 nm ($\lambda_{ex}$=283 nm) (FIG. 2A). Intrinsic wild-type fluorescence, as monitored at 331 nm upon an excitation at 283 nm, was linearly dependent on protein concentration (FIG. 2B). Although the P255 variants exhibited decreased fluorescence intensities, the same linear dependence between intrinsic protein fluorescence and protein concentration was observed (data not shown). The decrease in intrinsic fluorescence intensity suggests that the mutations induced changes in protein conformation, which agrees with a previous proposal based on the analysis of structural models for the wild-type enzyme and variants.

The equilibrium constant for NMPP binding to ferrochelatase could be determined from the change in intrinsic protein fluorescence upon ligand addition. Because incubation of ferrochelatase with NMPP resulted in reduction of intrinsic protein fluorescence, the dissociation constant of NMPP for either ferrochelatase or the P255 variants was estimated by titration of the enzyme with NMPP and quantification of the quenching effect. While the value for the dissociation constant ($K_d$) of NMPP to wild-type ferrochelatase was 9±5 nM, values for the variants increased by one order of magnitude with a $K_d$ of 0.16±0.07 µM for P255R and $K_d$ of 0.30±0.10 µM for P255G (FIG. 3). In fact, the order of magnitude of the affinity of wild-type ferrochelatase towards NMPP corroborates the results of previous studies on inhibition of bovine ferrochelatase by NMPP. However, the stability of the ferrochelatase-NMPP complex was clearly diminished by the substitutions of loop residue P255. The lower affinity of the mutated enzymes for NMPP could have resulted from altered positioning of NMPP in the porphyrin-binding site and, consequently, a weakened interaction between ligand and protein. Binding of N-methyl mesoporphyrin to *B. subtilis* ferrochelatase promotes a conformational change with widening of the binding cleft. A loop covering residues 221-233 (i.e., murine residues 248-259) and the N-terminal loop flanked by helices 1 and 2 appear to be the major participants in the adopted "open" conformation; thus mutations introduced in the P255 position most likely disrupt the interaction between NMPP and the protein. Alternatively, the loop might have a role in molecular recognition. Of the eight possible isomers of NMPP with different non-planar distortions of the macrocycle, only one specific isomer was complexed with wild-type *B. subtilis* ferrochelatase. The methyl group of the selected isomer was attached to the pyrrole ring A and positioned above the mean plane of the macrocycle. Since the present study was performed with commercially available NMPP, which is a racemic mixture of the eight isomers, the possibility that mutation of P255 alters the geometry of the binding site and the selectivity of the enzyme towards the NMPP isomer cannot presently be ruled out.

Kinetics of NMPP Inhibition.

Figure 4:
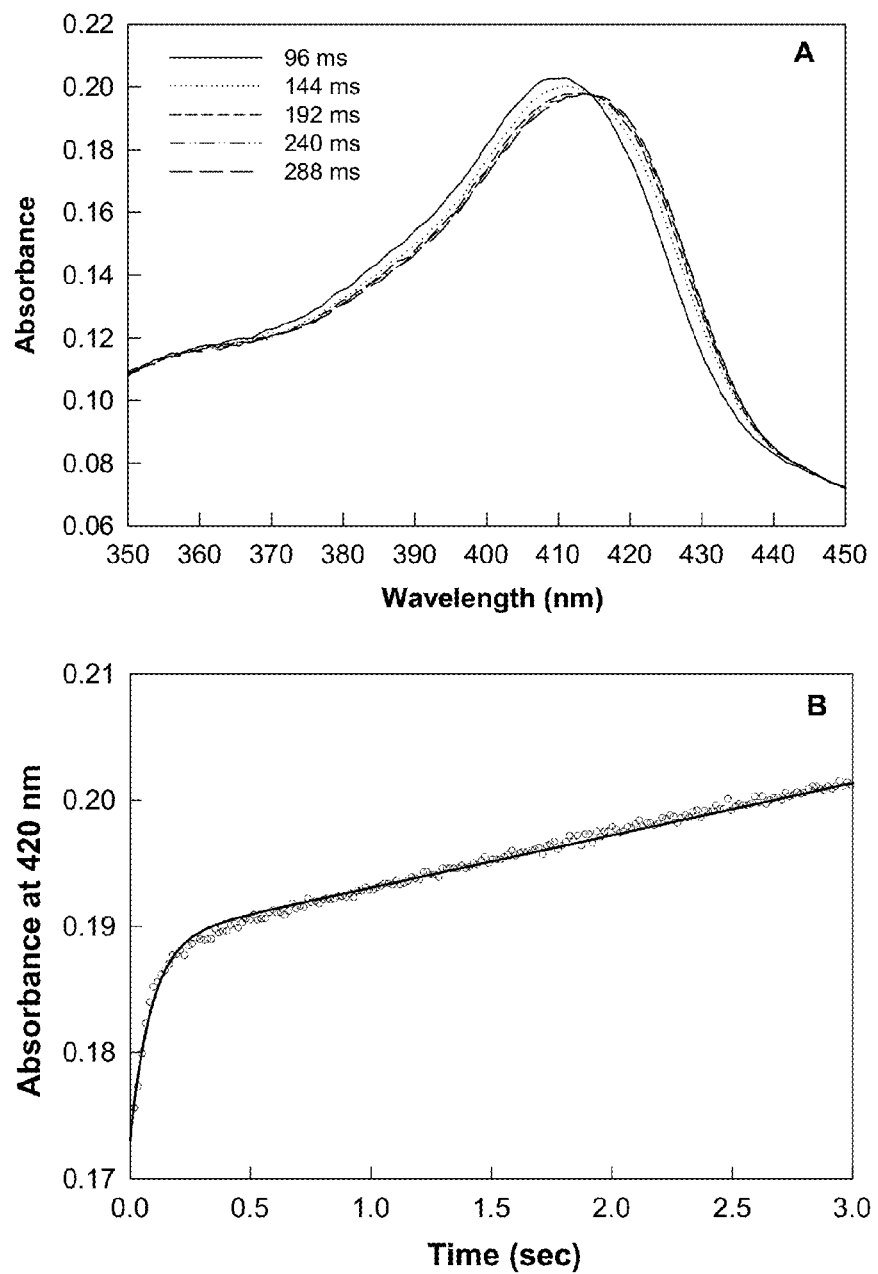
FIG. 4 shows transient kinetic analysis of the ferrochelatase-catalyzed reaction. Purified variant P255R (2 µM) was pre-incubated with protoporphyrin (10 µM) in 100 mM Tris-acetate, pH 8 containing 0.5% Tween-80. The solution was mixed with zinc-acetate (15 µM) to initiate the enzymatic reaction. A. Selected pre-steady state spectra from the 3000 spectra collected during the reaction. Spectra were collected at 96 ms, 144 ms, 192 ms, 240 ms and 288 ms since the inception of the reaction. B. Time course of the reaction at 420 nm, which records zinc-protoporphyrin formation. The collected data (open circles) were fitted to Equation 4 to obtain the rate constant k.

For some enzymes, such as thrombin and pyruvate dehydrogenase, a two-step binding mechanism has been invoked to characterize the enzymatic inhibition by certain substrate analogs. The high affinity of the enzyme towards the inhibitor has been related to the slow, second kinetic step corresponding to the rearrangement of the initial, weak enzyme-inhibitor complex into a more stable enzyme-inhibitor complex. To evaluate the kinetic pathway for inhibition of ferrochelatase and variants by NMPP, the kinetic steps involved in NMPP binding to the enzymes were investigated by monitoring the enzymatic reaction with $Zn^{2+}$ and protoporphyrin as substrates using rapid, scanning stopped-flow absorbance spectroscopy. FIG. 4A illustrates representative spectra from the 3,000 spectra (350-450 nm) collected for the P255R-catalyzed reaction in the absence of NMPP. The clear isosbestic point (at 412 nm) indicated inter-conversion between the two absorbing species, protoporphyrin and zinc-protoprophyrin (FIG. 4A), and thus the progress of the reaction could be monitored by following the formation of zinc-protoprophyrin. The time course for the first three seconds of the reaction records a pre-steady state burst of zinc-protoporphyrin production, followed by steady-state turnover (FIG. 4B). The presence of a burst of zinc-protoporphyrin formation implies that a step occurring after catalysis, which the inventors assign to product release, is at least partially rate-limiting.

Figure 5:
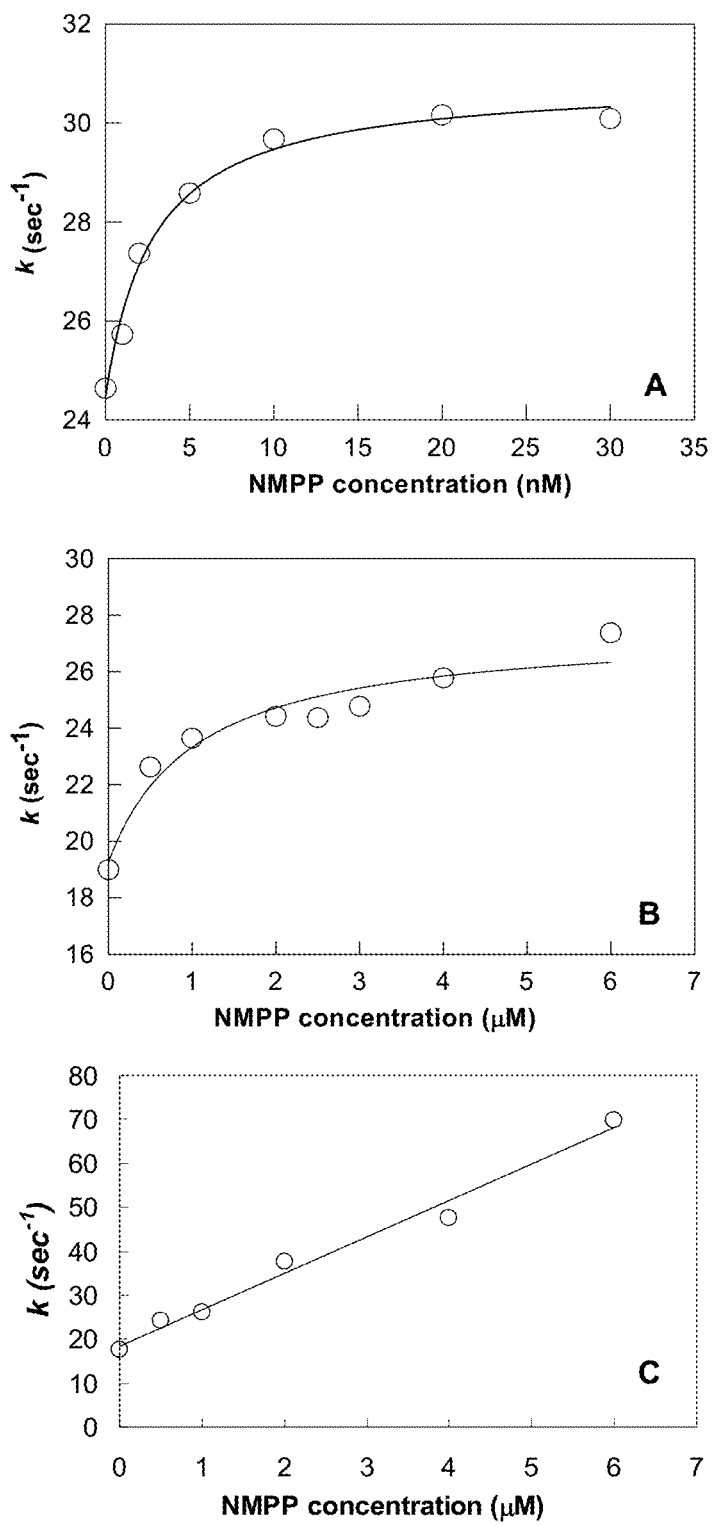
FIG. 5 shows the concentration dependence of the rate constants of NMPP binding to either ferrochelatase or P255 variants. Enzyme (0.5 µM) was reacted with protoporphyrin (5 µM) and zinc-acetate (15 µM) in the presence of various concentrations of NMPP. The pseudo first-order rate constant k was obtained from analysis of the time course (see Materials and Methods and FIG. 4) and plotted against NMPP concentration. The enzymes used in each set were: A. wild-type ferrochelatase; B. variant P255R; C. variant P255G.

In order to obtain the pseudo first-order rate constants for NMPP binding, the kinetic traces for zinc-protoporphyrin formation in the presence of various concentrations of inhibitor were fitted to equation 3. The hyperbolic nature of the pseudo-first order rate constant dependence on the inhibitor concentration suggests that NMPP binds to wild-type ferrochelatase (FIG. 5A) and P255R variant (FIG. 5B) via a two-step pathway with a kinetically significant intermediate (Scheme 1). The first step is assumed to involve the formation of an initial complex ([FC.NMPP]$_1$), which subsequently is rearranged into a more stable complex ([FC.NMPP]$_2$). Hence the second step of the kinetic pathway is likely to be associated with a slow conformational change of the inhibitor-protein complex. The data were fit to equation 1 for a two step process:

$$k = k_{-2} + \frac{k_2 I_0}{I_0 + K_i\left(1 + \frac{S_0}{K_m}\right)} \quad \text{(Eq. 1)}$$

where k is the pseudo first-order rate constant for the approach to the steady-state phase, $I_0$ is the inhibitor concentration, $S_0$ is the initial substrate concentration, $$K_i\left(1 + \frac{S_0}{K_m}\right)$$

is the apparent inhibition constant, $K_i^{app}$, and $k_2$ and $k_{-2}$ are the second step forward and reverse rate constants, respectively. The best fit of the points for the reaction with the wild-type enzyme (FIG. 5A) gave values of $k_2$=6.4 s$^{-1}$, $k_{-2}$=24.5 s$^{-1}$ and $K_i^{app}$=3 nM, while the fitting of the data for the reaction with the P255R variant returned values of $k_2$=8.3 s$^{-1}$, $k_{-2}$=19.3 s$^{-1}$ and $K_i^{app}$=1 µM. A two kinetic step process for binding of NMPP to either wild-type ferrochelatase or P255R (i.e., a fast, initial step for NMPP binding to the enzyme, followed by a slow step, possibly related to a conformational rearrangement of the protein-inhibitor complex) is consistent with the porphyrin-triggered conformational change of the active-site pocket deduced from the analysis of the crystal structure of *B. subtilis* ferrochelatase with bound N-methyl mesoporphyrin in comparison with that of the unliganded protein. Although the loop residues (248-259, murine numbering vis. 221-233 yeast numbering) are involved in the porphyrin-induced, wild-type protein conformational change, the values for the forward and reverse rate constants of the second step ($k_2$ and $k_{-2}$), which is rate-limiting in the 2-step binding pathway, were comparable between the P255R and wild-type enzymes. Therefore the diminished inhibition of variant P255R by NMPP ($K_i^{app}$=1 µM vs. $K_i^{app}$=3 nM for wild-type ferrochelatase) cannot be accounted for by differences in these rates.

In contrast to wild-type ferrochelatase and the P255R variant, the linear dependence of the pseudo-first order rate constant for NMPP binding to P255G on the inhibitor concentration (FIG. 5C) suggests that NMPP binds to the P255G variant via a single one-step process (Scheme 2). The pseudo-first order rate constant dependence on NMPP concentration was best described by equation 2:

$$k = k_{-1} + \frac{k_1 I_0}{1 + \frac{S_0}{K_m}} \quad \text{(Eq. 2)}$$

where $$\frac{k_1}{1 + \frac{S_0}{K_m}}$$

and $k_{-1}$ are the forward and reverse rate constants, respectively. By fitting the data displayed in FIG. 5C to equation 2, the forward and reverse rate constants were determined to be 8.2 µM$^{-1}$ s$^{-1}$ and 18.7 s$^{-1}$, respectively, while resolution of $$\frac{k_{-1}}{k_1}\left(1 + \frac{S_0}{K_m}\right)$$

yielded a value for $K_i^{app}$ of 2.3 µM. Although NMPP binding to P255G occurred via a one-step reaction, the values for the rate constants associated with this step ($k_1$ and $k_{-1}$) were similar to those determined for the rate-limiting step of the kinetic pathway for inhibition of ferrochelatase and P255R by NMPP. This suggests that the rate of NMPP binding was unlikely to contribute to its lessened inhibitory effect on P255G.

While the binding affinity of the P255 variants for NMPP was one order of magnitude lower than that of the wild-type protein ($K_d$ values of 0.16 µM and 0.30 µM vs. 9 nM), the inhibition constant increased by approximately two orders of magnitude ($K_i^{app}$ values of 1 µM and 2.3 µM vs. 3 nM). These results suggest the P255 residue is involved in conferring specificity towards the recognition of N-alkylated porphyrins. Indeed, the loop residues were previously proposed to function in specifically orienting the porphyrin vinyl substituents and probably the entire porphyrin macrocycle.

Analysis of resonance Raman spectra revealed an enhancement of the vinyl stretching band $v_{Ca=Cb}$ of Ni-protoporphyrin upon binding to either ferrochelatase or loop variants. Additionally, changes in the vinyl-related lines of hemin bound to the P255R and P255G variants were also observed when compared to those of wild-type ferrochelatase-bound hemin. In particular, a downshift of the core-size marker $v_2$ for hemin bound to P255R and P255G indicated that the porphyrin ring was even more expanded than when hemin was bound to wild-type ferrochelatase. These results again implicate a mechanism of recognition and interaction between the loop residues, including P255, and the porphyrin ring.

Size Measurement of the Active Site Pocket.

In order to compare the size of the active site in the P255 variants with that of wild-type ferrochelatase, the volume and Connolly's surface area of the porphyrin-binding pocket in the structural models were estimated using the program CAST. The active site of wild-type ferrochelatase was found to occupy a surface area of 2138 Å$^2$ and a volume of 3015 Å$^3$, while variant P255R had a smaller surface area of 1340 Å$^2$ and a reduced volume of 1932 Å$^3$, and variant P255G had a surface area of only 1048 Å$^2$ and a volume of 1604 Å$^3$. Thus, the binding pocket size was significantly reduced as a result of the P255 mutations. Variant P255R retained ~70% of the volume and surface area relative to the wild-type protein, whereas P255G only kept ~50% of the size of the wild-type porphyrin-binding pocket. Previous structural modeling of variants with mutated loop residues suggested that loop mutations affect the active site architecture (Shi and Ferreira 2004). Based on the measurements of the porphyrin-binding pocket and previous structural modeling of loop variants, P255 residue appears to have a crucial role in supporting an open conformation of the active site in wild-type ferrochelatase. In contrast, the P255 variants are possibly impaired to widen the active-site cleft, leading to a restricted NMPP entry and decreased binding affinity. This possibility is consistent with the function of proline as a conformational switch, as demonstrated in a variety of proteins such as interleukin-2 tyrosine kinase and Hsp70 chaperones. On the other hand, the regiospecificity of porphyrin binding is critical to ferrochelatase function and any variation of the steric characteristics of the active site of the enzyme will most certainly affect the binding affinity for NMPP. In 1981, Ortiz de Montellano et al. demonstrated that the potency of N-alkyl protoporphyrin structures as to inhibit ferrochelatase depends on the specific location of the N-alkyl group on the porphyrin ring. Isomers with the N-alkyl group on pyrrole rings A or B were significantly much stronger (i.e., 30-100 times) than those with the N-alkyl group on pyrrole rings C or D. In fact, the authors reported that "the identity of the nitrogen alkylated in the protoporphyrin IX is a major determinant of the inhibitory activity". How stereoselective inhibition of ferrochelatase by N-alkylated porphyrin is achieved was further investigated to prove that, within the ring A-substituted (NA) and the ring B-substituted (NB) regioisomers and enantiomers of N-ethyl-protoporphyrin, the NA regioisomer and the epi-NB isomer were the more potent inhibitors of ferrochelatase. Therefore, the greater inhibitory activity of these two isomers probably reflected their macrocycle non-planar distortions being more on a par with that undergone by the porphyrin substrate during ferrochelatase-catalyzed porphyrin metallation. In other words, the NA and the epi-NB isomers were stronger inhibitors because they were more effective as transition state analogues of the ferrochelatase-catalyzed reaction. Clearly the regiospecificity of ferrochelatase for N-alkylated porphyrins, including NMPP, mirrors defined interactions between porphyrin and protein. Mutation of P255 in murine ferrochelatase could have disrupted this interaction and/or altered the stereospecificity of the enzyme towards NMPP.

Despite the marked differences with respect to NMPP binding, the variants exhibited steady-state kinetic properties similar to those of the wild-type enzyme. While wild-type ferrochelatase had a $k_{cat}$ of 4.1±0.3 min$^{-1}$, the catalytic activity was slightly increased in the variants, with values of $k_{cat}$ of 7.8±0.8 min$^{-1}$ for P255R and 5.9±1.4 min$^{-1}$ for P255G. The $K_m^{PPIX}$ value for the wild-type enzyme was 1.4±0.2 μM, and it was slightly greater in the variants, with values of 2.65±0.44 μM for P255R and 2.51±0.80 μM for P255G. Thus, the specificity constant for protoporphyrin, i.e., $k_{cat}/K_m^{PPIX}$, was 2.92 min$^{-1}$μM$^{-1}$ for wild-type ferrochelatase, 2.94 min$^{-1}$μM$^{-1}$ for P255R and 2.35 min$^{-1}$μM$^{-1}$ for P255G. These results imply that specificity towards the physiological protoporphyrin IX substrate is distinct from the observed selectivity towards NMPP. One possible explanation for these findings is that the mechanism of interaction between the enzyme and the protoporphyrin substrate differs from that for inhibitor binding. It is conceivable that the active site of ferrochelatase is optimized for interaction with the protoporphyrin substrate and retains a certain degree of plasticity towards this end. Possibly, this facilitates the induction of porphyrin deformation in the protein matrix, and in so doing, ensures the catalytic reaction to proceed. In contrast, the constraints of the active site towards NMPP are presumably more stringent than towards the protoporphyrin substrate and any alterations of the active site affect the selectivity towards NMPP. Another possible explanation, and not necessarily mutually exclusive from the former, is that mutations introduced in the active site (e.g., at the P255 position) cause an alteration of the regiospecificity of ferrochelatase, such that the mutated active site can accommodate either a regioisomer or a combination of regiosisomers of NMPP different from those of the wild-type active site. It is worth noting that 1) the commercially available NMPP used in this study consists of a racemic mixture of the eight potential isomers and 2) only one NMPP isomer was identified in the crystal structure of the B. subtilis ferrochelatase. The final answer to the question of whether P255R and P255G exhibit different stereospecificity and bind a different NMPP stereoisomer awaits the determination of the crystal structures of the complexes between NMPP and P255R (or P255G).

Finally, heme deficiency has been recently reported to be associated with various disorders, such as Alzheimer's disease, frataxin-deficiency mediated diseases and oxidative damage resulted from hyperoxia. In these studies, NMPP treatment of cultured cells has provided a convenient model system to induce heme deficiency. Typically, NMPP-treated cells exhibit impaired enzymatic activity and assembly of the mitochondrial electron transport complex IV, i.e., cytochrome c oxidase (COX). COX has been proposed to have a cytoprotective role by removing reactive oxygen species and its deficiency renders cells more susceptible to oxidative stress. Thus, the ferrochelatase variants with improved tolerance towards NMPP can be used in cell assay systems to study physiological responses to heme deficiency. It will be possible to determine whether the observed NMPP-induced cytotoxicity could be alleviated by expressing constitutively either of the P255 variants; these variants would confer resistance to NMPP inhibition and thereby keep heme synthesis uninterrupted.

SCHEME 1

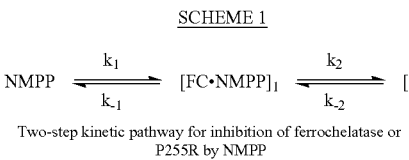

Two-step kinetic pathway for inhibition of ferrochelatase or P255R by NMPP

SCHEME 2

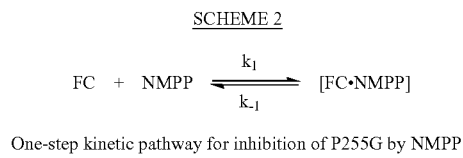

One-step kinetic pathway for inhibition of P255G by NMPP

EXAMPLE

Reagents. Trisamino-methane carbonate (Trizma base), polyethylene glycol sorbitan monooleate (Tween-80), polyethylene glycol sorbitan monolaurate (Tween-20) and zinc acetate were obtained from Sigma Chemicals. TALON metal affinity resins were purchased from BD Biosciences. E. coli strain Δvis was a kind gift of Dr. H. Inokuchi at Kyoto University (Nakahigashi et al. 1991).

Genetic Selection in E. coli. E. coli Δ vis cells harboring plasmids encoding active, ferrochelatase variants isolated from a random sequence library of the loop motif were grown 16-18 h at 37° C. in LB agar medium containing 50 μg/mL of ampicillin and varying concentrations of NMPP. For the preparation of the NMPP-containing LB-ampicilin agar plates, a 2 mM stock solution of NMPP was made by dissolving NMPP in 20 mM NH4OH containing 2% Tween-20. The solution was filter-sterilized and kept at 4° C. The stock solution was diluted 100-, 1000- and 10000-fold to prepare LB-ampicilin plates containing 20 μM, 2 μM and 0.2 μM NMPP. A vis cells transformed with wild-type ferrochelatase and functional variants were grown in LB medium containing 50 μg/mL ampicilin and 0.4% (w/v) glucose at 37° C., overnight, with shaking at 220 RPM. Each of the overnight cultures was diluted 20-fold into fresh medium and grown at 37°

C. for ~1 hr until OD600 reached ~0.4-0.5. Subsequently, these cultures were diluted with LB medium by 106 and 100 μl aliquots of the diluted stock were spread on LB-ampicilin agar plates and LB-ampicilin agar plates containing NMPP at 0.2 μM, 2 μM and 20 μM, respectively. The plates were incubated at 37° C. for 16 hr, and the colonies on each plate were counted. Thus, NMPP-resistant clones or clones more tolerant to NMPP than wild-type ferrochelatase could be selected.

Protein Purification. Wild-type, murine ferrochelatase and variants were over-expressed, under the control of the E. coli alkaline phosphatase promoter phoA, in BL21(DE3) cells. The purification of the recombinant proteins bearing a N-terminal penta-histidine tag, assessment of the purity by sodium dodecyl sulfate-polyacrylamide gel electrophoresis and determination of protein concentration and enzymatic activity were as described previously (Shi and Ferreira 2004).

Fluorescence Titration Measurements. Equilibrium fluorescence measurements were made using a Shimadzu RF-5301PC fluorimeter at 23° C. with excitation and emission wavelengths at 283 nm and 331 nm, respectively. The decrease in protein fluorescence, due to NMPP binding, was monitored. Purified wild-type ferrochelatase or variants, P255R and P255G, were diluted into 3 mL of 10 mM Tris-acetate, pH 8, containing 0.05% Tween-80, and a stock solution of NMPP at 200 μM was made by dissolving NMPP in 100 mM $NH_4OH$ containing 0.5% Tween-80. In a typical titration experiment, aliquots of the NMPP stock were added to the protein solution and, upon incubation on ice for 1 h, the quenching in fluorescence was monitored as described above. The concentration of the protein was maintained low in relation to the $K_d$ value in order to guarantee an accurate determination of the dissociation constant. The observed fluorescence intensity was plotted against NMPP concentration and the dissociation constant of NMPP for ferrochelatase was determined using the least-squares fit of each data set to equation 3 by nonlinear regression:

$$F = F_0 - \frac{\Delta F\left[(E_t + L + K_d) - \sqrt{(E_t + L + K_d)^2 - 4E_t L}\right]}{2E_t} \quad \text{(Eq. 3)}$$

where $K_d$ is the dissociation constant, F is the measured fluorescence, $F_0$ is the fluorescence in the absence of NMPP, $\Delta F$ is the total change in fluorescence, $E_t$ is total protein concentration, and L is the total NMPP concentration.

Transient Kinetic Analysis. The kinetic steps involved in NMPP binding to ferrochelatase were assessed using stopped-flow absorption spectroscopic analysis by monitoring the enzymatic reaction in the presence of various concentrations of the inhibitor NMPP. The reactions were performed using a rapid scanning stopped-flow spectrophotometer (model RSM-1000; OLIS Inc.), equipped with a stopped-flow mixer and an observation chamber with an optical pathlength of 4 mm. The dead time of the instrument is ~2 ms. Scan spectra spanning the wavelength range of 347 to 574 nm were collected at a rate of 1000 scan/sec. The syringes containing the reaction components and the stopped-flow cell were maintained at 30° C. using an external water-bath. The concentrations of reagents loaded into each syringe were two-fold greater than the final concentrations in the observation chamber. Enzymatic activity was monitored by following the increase in absorbance at 420 nm for zinc-protoporphyrin production using $Zn^{2+}$ and protoporphyrin as substrates.

The enzyme and substrate stock solutions were diluted in 100 mM Tris-acetate, pH 8.0, containing 0.5% Tween-80. The stock solutions for substrates and inhibitor were prepared as follows: A 3 mM zinc-acetate solution was made by dissolving zinc-acetate in distilled and deionized $H_2O$. A 200 μM protoporphyrin solution was prepared by dissolving protoporphyrin IX in 50 mM $NH_4OH$ containing 0.5% Tween-80. A 2 mM NMPP solution was prepared by dissolving NMPP in 100 mM $NH_4OH$ containing 0.5% Tween-80. Typically, a 2 mL solution that was 1 μM in ferrochelatase and 10 μM in protoporphyrin was pre-incubated on ice for 30 min. The porphyrin-enzyme solution was titrated with NMPP. The mixture was subsequently transferred to one of the stopped-flow syringes. The other stopped-flow syringe was loaded with a reaction buffer solution of ~2 mL that was 30 μM in zinc-acetate. The enzymatic reaction was initiated by mixing the contents from both syringes and reaction progression was monitored by following the increase in absorbance at 420 nm. The data were analyzed by fitting the observed absorbance values to equation 4:

$$A = A_0 + v_s t + \frac{v_0 - v_s}{k}(1 - e^{-kt}) \quad \text{(Eq. 4)}$$

where A is the observed absorbance, $A_0$ is the initial absorbance, $v_s$ is the steady-state velocity, $v_0$ is the initial velocity and k is the pseudo-first order rate constant for inhibitor binding. Equation 4 describes the progress of enzymatic reactions in the presence of tight-binding competitive inhibitors.

Measurement of Ligand Binding Pocket Size. Structural models for wild-type, murine ferrochelatase and variants P255R and P255G were generated using the amino acid sequence and coordinates for human ferrochelatase (Protein Data Bank accession code 1hrk) as the template. Sequence alignments, molecular modeling, energy minimization and model analysis using PROCHECK were performed on the Geno3D servers at the Institute of Biology and Chemistry of Proteins (IBCP) in France (Combet et al. 2002). Dimensions of the porphyrin binding pocket in the monomeric models of wild-type ferrochelatase and variants were calculated on the CASTp server (Liang et al. 1998). Values for the area and volume of Connolly's surface of the active site cavity were determined using the CAST program.

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned, as well as those inherent therein. The examples provided here are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A cellular model to determine physiological responses to heme deficiency comprising:
   an isolated host cell expressing a ferrochelatase variant enzyme;
   wherein the ferrochelatase variant enzyme has a mutation in the ferrochelatase enzymatic active-site loop wherein there are no alterations outside of the ferrochelatase enzymatic active-site loop.

2. The cellular model of claim 1, wherein PRO$^{255}$ of the ferrochelatase variant is replaced with an amino acid selected from the group consisting of arginine and lysine.

3. The cellular model of claim 1, comprising a mutation in the ferrochelatase enzymatic active-site loop wherein Pro$^8$ of SEQ ID NO: 1, 2, 3, 7, 8, 9 or 10 is replaced with arginine.

4. The cellular model of claim 2, wherein the active site of the ferrochelatase variant has a surface area of about 1340 angstroms$^2$ and a volume of about 1932 angstroms$^3$.

5. The cellular model of claim 2, wherein the ferrochelatase variant has a volume of about 70% of the wild-type ferrochelatase.

6. The cellular model of claim 1, wherein the active site of the ferrochelatase variant has a surface area of about 1048 angstroms$^2$ and a volume of about 1604 angstroms$^3$.

7. The cellular model of claim 1, wherein the ferrochelatase variant has a volume of about 50% of the wild-type -ferrochelatase.

* * * * *

SEQUENCE LISTING

<160> NUMBER OF SEQ ID NOS: 12

<210> SEQ ID NO 1
<211> LENGTH: 10
<212> TYPE: PRT
<213> ORGANISM: Mus musculus

<400> SEQUENCE: 1

Gln Ser Lys Val Gly Pro Val Pro Trp Leu
1               5                   10

<210> SEQ ID NO 2
<211> LENGTH: 10
<212> TYPE: PRT
<213> ORGANISM: Homo sapiens

<400> SEQUENCE: 2

Gln Ser Lys Val Gly Pro Met Pro Trp Leu
1               5                   10

<210> SEQ ID NO 3
<211> LENGTH: 10
<212> TYPE: PRT
<213> ORGANISM: Gallus gallus

<400> SEQUENCE: 3

Gln Ser Lys Val Gly Pro Met Pro Trp Leu
1               5                   10

<210> SEQ ID NO 4
<211> LENGTH: 10
<212> TYPE: PRT
<213> ORGANISM: Drosophila melanogaster

<400> SEQUENCE: 4

Gln Ser Lys Val Gly Pro Leu Ala Trp Leu
1               5                   10

<210> SEQ ID NO 5
<211> LENGTH: 10
<212> TYPE: PRT
<213> ORGANISM: Arabidopsis thaliana

<400> SEQUENCE: 5

Gln Ser Arg Val Gly Pro Val Gln Trp Leu
1               5                   10

<210> SEQ ID NO 6
<211> LENGTH: 10
<212> TYPE: PRT
<213> ORGANISM: Hordeum vulgare

<400> SEQUENCE: 6

Gln Ser Arg Val Gly Pro Val Gln Trp Leu
1               5                   10

<210> SEQ ID NO 7
<211> LENGTH: 10
<212> TYPE: PRT
<213> ORGANISM: Saccharomyces cerevisiae

<400> SEQUENCE: 7

Gln Ser Gln Val Gly Pro Lys Pro Trp Leu
1               5                   10

```
<210> SEQ ID NO 8
<211> LENGTH: 10
<212> TYPE: PRT
<213> ORGANISM: Schizosaccharomyces pombe

<400> SEQUENCE: 8

Gln Ser Lys Val Gly Pro Leu Pro Trp Met
1               5                   10

<210> SEQ ID NO 9
<211> LENGTH: 10
<212> TYPE: PRT
<213> ORGANISM: Escherichia coli

<400> SEQUENCE: 9

Gln Ser Arg Phe Gly Arg Glu Pro Trp Leu
1               5                   10

<210> SEQ ID NO 10
<211> LENGTH: 10
<212> TYPE: PRT
<213> ORGANISM: Yersinia enterocolitica

<400> SEQUENCE: 10

Gln Ser Arg Phe Gly Arg Glu Pro Trp Leu
1               5                   10

<210> SEQ ID NO 11
<211> LENGTH: 11
<212> TYPE: PRT
<213> ORGANISM: Thermus thermophilus

<400> SEQUENCE: 11

Gln Ser Ala Gly Arg Thr Pro Glu Pro Trp Leu
1               5                   10

<210> SEQ ID NO 12
<211> LENGTH: 11
<212> TYPE: PRT
<213> ORGANISM: Bacillus subtilis

<400> SEQUENCE: 12

Gln Ser Glu Gly Asn Thr Pro Asp Pro Trp Leu
1               5                   10
```